United States Patent [19]

Laruelle et al.

[11] 4,415,574
[45] Nov. 15, 1983

[54] NOVEL SOLUBLE $N_2$ SUBSTITUTED DERIVATIVES OF 2,4-DIAMINO 5-BENZYL PYRIMIDINE, PROCESS FOR THEIR PREPARATION AND MEDICAMENTS CONTAINING THEM

[75] Inventors: Claude Laruelle, Villeneuve Loubet; Marcel Lepant, Vence, both of France

[73] Assignee: S. A. Panmedica, Carros, France

[21] Appl. No.: 358,260

[22] Filed: Mar. 15, 1982

[30] Foreign Application Priority Data

Mar. 20, 1981 [FR] France .................. 81 05592

[51] Int. Cl.³ .................. C07D 239/49; C07D 401/12; A61K 31/505
[52] U.S. Cl. .................. 424/251; 544/324; 544/325
[58] Field of Search .................. 544/324, 325; 424/251

[56] References Cited

U.S. PATENT DOCUMENTS 4,232,023 11/1980 Dick .................. 544/325

FOREIGN PATENT DOCUMENTS 2358148 2/1978 France .
2397407 2/1979 France .

*Primary Examiner*—Mary C. Lee
*Attorney, Agent, or Firm*—Browdy and Neimark

[57] ABSTRACT

The present invention relates to novel soluble $N_2$ substituted derivatives of 2,4-diamino 5-benzyl pyrimidines. These derivatives correspond to the general formula III below:

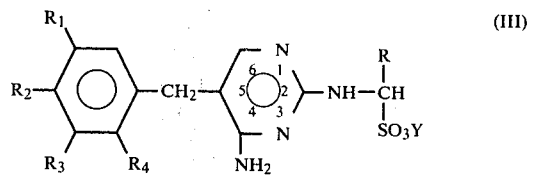

The novel soluble $N_2$ substituted derivatives are powerful antibacterial agents.

39 Claims, No Drawings

SOLUBLE N₂ SUBSTITUTED DERIVATIVES OF 2,4-DIAMINO 5-BENZYL PYRIMIDINE, PROCESS FOR THEIR PREPARATION AND MEDICAMENTS CONTAINING THEM

FIELD OF THE INVENTION

The present invention relates to novel soluble $N_2$ substituted derivatives of 2,4-diamino 5-benzyl pyrimidine, the process for their preparation and to medicaments containing them. 2,4-diamino 5-(3,4,5-trimethoxybenzyl)pyrimidine has long been known (U.S. Pat. No. 3,049,544 of 1962) as a very wide-spectrum antibacterial agent encompassing both Gram-positive cocci and Gram-negative cocci and Gram negative bacilli. Its mechanism of action approaches that of the sulfamides, it interferes with dehydrofolate-reductase, which enzyme plays a part in the reduction of folic acid, a metabolite necessary for synthesis of thymine. It acts at a later stage than the sulfamides to inhibit synthesis of folic acid. This explains its synergistic action with sulfamides.

DESCRIPTION OF THE PRIOR ART

Unfortunately, this products is very slightly soluble in water and it is very difficult to prepare, for example, injectable solutions. To achieve these recourse is had, either to suspensions (for example French Pat. No. 2,085,703) or to organic solvents. Very great progress in this direction has been made by means of the work of MM. Rombi and Dick (French Pat. Nos. 2,358,148 and 2,397,407). The synthetic products obtained, namely the $N_2N_4$ substituted derivatives of formula I:

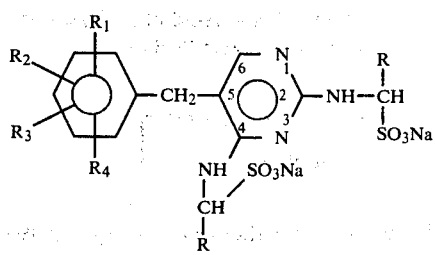

or the $N_4$ substituted derivatives of the formula II:

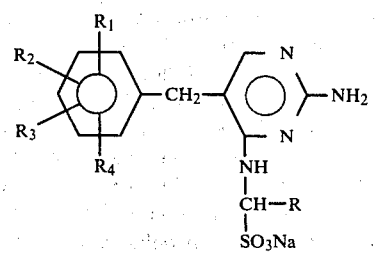

although very soluble in water, have however still two kinds of drawbacks:
- the products obtained are never chemically pure, but constitute a variable mixture of the $N_2N_4$ disubstituted and $N_4$ monosubstituted derivatives,
- their stability at acid pH's leaves somthing to be desired and they are hence difficultly purifiable.

GENERAL DESCRIPTION OF THE INVENTION

According to the present invention there are provided novel soluble $N_2$ substituted derivatives of 2,4-diamino 5-benzyl pyrimidine corresponding to the formula III below:

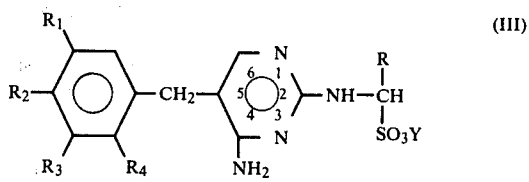

in which:
$R_1$, $R_2$, $R_3$, $R_4$ which can be identical or different represent a hydrogen atom, a halogen atom, or an alkyl thioalkyl alkoxy or benzyloxy group,
Y represents a hydrogen atom, an alkali metal or a pharmaceutically compatible organic base, and
R represents a hydrogen atom or a linear or branched alkyl radical comprising from 1 to 7 carbon atoms, a cycloalkyl radical comprising 5 to 8 carbon atoms, an aromatic nucleus possibly substituted by substituents such as halogen, nitro-, hydroxyl, dialkylamino-, alkoxy-, alkyl from $C_1$ to $C_3$, two adjacent substituents being able to constitute an alkyldioxy ring, a heterocyclic ring like furane, thiophene, or pyridine.

Among the derivatives of 2,4-diamino pyrimidine, may be mentioned, preferably, 5-(3,4,5-trimethoxy benzyl) 2,4diamino pyrimidine or trimethoprime, 5-(3,4dimethoxy benzyl) 2,4diamino pyrimidine or diaveridine, 5-(2-methyl 4,5-dimethoxy benzyl) 2,4-diamino pyrimidine or ormethoprime.

Apart from the complete stability and analytical purity of the products obtained, Applicant has also observed surprisingly, that the activity of the products according to the present invention is much higher than that of the $N_2N_4$ or $N_4$ substituted products.

According to another aspect of the invention there is provided a process for the preparation of these products of formula III according to the invention, comprising reacting a derivative of 2,4-diamino5-benzyl pyrimidine with an aldehyde and sulfurous anhydride, in a suitable solvent such as pyridine particularly and then isolating the product of the reaction.

According to an advantageous embodiment of the process according to the present invention, the amount of 2,4-diamino 5-benzyl pyrimidine and of aldehyde are stoichiometric, whilst the sulfurous anhydride is used in excess.

According to another advantageous embodiment of the process according to the present invention, the product of the reaction is isolated by dilution of the reaction medium with a pyridine miscible solvent such as ether or a hydrocarbon.

According to a particular modification of this embodiment, the product isolated is in addition purified by washing with aqueous alcohol.

According to another aspect of the present invention then are provided water-soluble medicaments containing at least one derivative according to the present invention.

In fact, these derivatives are very soluble in water and enable the production of aqueous solutions containing up to 50% weight/volume. The products obtained are white microcrystalline powders, stable in their acid or salt forms. The aqueous solutions of the salts are in the form of a colorless transparent liquid and with a pH close to neutrality.

Besides the foregoing features, the invention comprises still other features which will emerge from the description which follows.

The invention is aimed particularly at novel $N_2$ substituted derivatives of 2,4-diamino 5-benzyl pyrimidine which are remarkably stable and very soluble in water, which are fully suited to the manufacture of injectable medicaments, as well as the means adapted to their production and to the practising of the manufacturing processes for these new derivatives.

The invention will be better understood on reading the additional description which follows, which refers to examples of manufacture, and analysis of the products obtained, as well as to an account of pharmacological experiments bearing on the medicaments according to the present invention.

It must be well understood however that these examples, the different analytical results and this account of pharmacological experiments, are given purely by way of illustration of the products and processes according to the invention, of which they do not constitute in any way a limitation thereof.

In the Examples which follow, the thin layer chromatography (TLC) was carried out on a KIESELGEL F 254 plate with development in UV light at 254 nm in the following migration systems:

System A: chloroform: 80, methanol: 20, acetic acid: 20—water: 1

System B: chloroform: 80—ethanol: 40 formic acid: 5

Trimethoprime has an Rf of 0.6 in system A and 0.3 in system B.

DESCRIPTION OF PREFERRED EMBODIMENTS

Example 1—$N_2$Methane Sulfonic Acid of 2,4-Diamino 5-(3,4,5-Trimethoxy Benzyl) Pyrimidine and its Sodium Salt

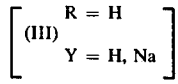

2.22 g (74 mM) of paraformaldehyde and 19.6 g (70 mM) of trimethoprime were added successively to 80 ml of pyridine and 70 g of sulfurous anhydride were introduced in two hours, the temperature being spontaneously maintained at 45°–50°. It was then taken to 80° C. for 8 hours. After cooling, there were run in 500 ml of ether and the precipitate separated. The precipitate was suspended in water and redissolved by the addition of dilute sodium hydroxide in a sufficient amount for pH=9.70. After filtration of a light insoluble substance, it was reprecipitated by the addition of dilute hydrochloric acid in sufficient amount for pH=½. The precipitate was filtered, washed abundantly with water then with ethanol. After drying, the acid form of the desired derivative was obtained in the pure state in the form of white crystals of mp 176° C. TLC gives an Rf of 0.33 in the system A and 0.16 in the system B. This acid form can be treated in an aqueous medium by dilute sodium hydroxide to a pH 9.50 to give the sodium salt which is isolated by evaporation and drying [mp higher than 250° C. (dec)] [NMR:2 H at 4.8 ppm (m)].

Example 2—$N_2$ Ethane Sulfonic acid of 2,4-Diamino 5-(3,4,5-Trimethoxy Benzyl) Pyrimidine

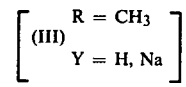

14.5 g (0.05 mole) of trimethoprime and 2.2 g (0.05 mole of acetaldehyde were added successively to 100 ml of pyridine. At the rate of about 10 g per hour, 40 g of sulfurous anhydride were introduced, and then it was brought to 60° C. for 8 hours. After cooling, it was run into 500 ml of ether, the precipitate was filtered and it was dried in air. The crude product was resuspended in water and treated with the dilute sodium hydroxide to a pH of 8.80. The light insoluble product was filtered off and the filtrate was then acidified by hilute hydrochloric acid of pH 2.50. The precipitate was filtered off, washed carefully with water, then ethanol. After drying, the desired derivative was obtained in the form of beautiful white crystals of mp 192° C. TLC gave a spot of Rf 0.43 in the system A and 0.31 in the system B. The acid form can be converted into its sodium salt by treatment of the aqueous suspension of the preceding product by a dilute sodium hydroxide to a pH of 8.80. After evaporation and drying, the sodium salt of the desired derivative of mp 178°/180° C. was obtained.

(NMR: $CH_3$ (d) 3 H at 0.3 ppm, CH (9m) 1 H at 4.7 ppm).

Example 3—$N_2$ Butane Sulfonic Acid of 2,4-Diamino 5-(3,4,5-Trimethoxy Benzyl) Pyrimidine

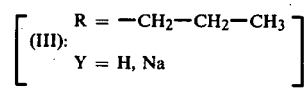

14.5 g (0.050 mole) of trimethoprime and 3.6 g (0.050 mole) of butyraldehyde were successively introduced into 200 ml of pyridine and about 45 g of sulfurous anhydride was introduced slowly with stirring. The reagents passed rapidly into solution, whilst the internal temperature rose spontaneously to 35°–40° C. to become stabilized. It was left for 24 hours at ordinary temperature then run into a liter of ether. The precipitate was filtered, washed with ether, and dried in air. The crude product was then placed in aqueous suspension and treated with dilute sodium hydroxide to a pH of 8.50. A light insoluble substance was filtered off and then it was acidified with dilute hydrochloric acid, to a pH 2.0; the acid form precipitates again in beautiful white crystals which are filtered and washed abundantly with water, then with ethanol. After drying, the acid form of the desired derivative of mp 165° C. was obtained. TLC gave an Rf of 0.50 in the A system and 0.40 in the B system. It is possible to place it in the acid form again in aqueous suspension and treat it with dilute sodium hydroxide to a pH of 8.50. After evaporation and drying, the sodium salt of the desired derivative of mp 180° C. was obtained (NMR: $CH_3$—$(CH_2)_2$ (m) 7 H to 1.3 ppm, CH (m) 1 H to 4.7 ppm).

Example 4—N₂ (2-Methyl) Propane Sulfonic Acid of 2,4-Diamino 5-(3,4,5-Trimethoxy Benzyl) Pyrimidine and its Sodium Salt

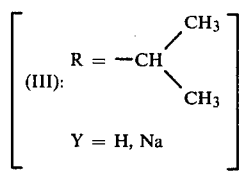

14.5 g (0.05 mole) of trimethoprime and 3.6 g (0.05 mole) of isobutyraldahyde was added to 100 ml of pyridine; then with stirring, about 45 g of sulfurous anhydride were introduced, and the temperature stabilized towards 40° C. After some hours at ordinary temperature, the solution was run into a large volume of ether. After isolation of the crude material, it was treated as previously by dissolving at a pH 9.0, some impurities were removed by filtration and it was reprecipitated with dilute hydrochloric acid. The acid form was then filtered, washed very carefully with water and then dried (mp=182° C.).

TLC gave a single spot of Rf 0.58 in the system A and 0.45 in the system B. It way possible to obtain the sodium salt by neutralization of the aqueous suspension of the acid form with dilute sodium hydroxide to a pH 9.20. The solution, after evaporation and drying, gave the salt form of mp 160° C. (NMR: CH₃ (d) 6 H at 1 ppm, CH (m) 1 H at 2.2 ppm, CH (m) 1 H at 4.8 ppm).

Example 5—N₂ (2,2-Dimethyl) Propane Sulfonic Acid of 2,4-Diamino 5-(3,4,5-Trimethoxy Benzyl) Pyrimidine

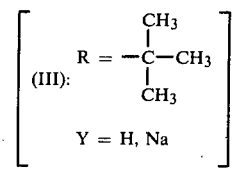

14.5 g (0.050 mole) of trimethoprime and 4.5 g (0.050 mole) of pivalic aldehyde was added successively to 100 ml of pyridine. After treatment according to the usual technique, the crude product was resuspended in 300 ml of water and made alkaline with dilute sodium hydroxide to pH 9.0. A light insoluble material was filtered off, and it was then acidified with dilute hydrochloric acid to pH 2.50. The precipitate which appeared was filtered off, it was washed abundantly with water, and then with ethanol. After drying, the acid form of the desired derivative of mp 170° C. was obtained. TLC only gave a single spot of Rf 0.70 in the A system and 0.55 in the B system. This product can be resuspended in water and by treatment with sodium hydroxide diluted at pH 8.70; after evaporation and drying, the sodium form of the desired derivative of mp=155° C. was obtained (NMR: CH₃ (s) 9 H at 1 ppm CH (m) 4.8 ppm).

Example 6—N₂ (2,3-Dimethyl) Pentane Sulfonic Acid of 2,4-Diamino 5-(3,4,5-Trimethoxy Benzyl) Pyrimidine and its Sodium Salt

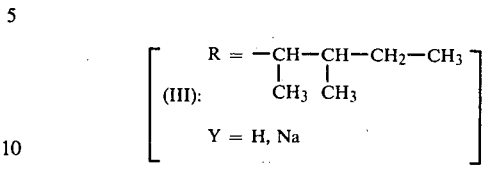

At ordinary temperature, 14.5 g (0.05 mole) of trimethoprime and 5.6 g (0.05 mole) of 2,3 dimethylvaleric aldehyde was added to 100 ml anhydrous pyridine, and then slowly with stirring, about 45 g of sulfurous anhydride was introduced. The reagents passed fairly rapidly into solution, whilst the internal temperature was stabilized between 35° and 40°. It was left to stand then for 24 hours at ordinary temperature, then run slowly into a liter of ether. The white precipitate which appeared immediately was filtered off, washed with ether, then dried. The product was replaced in aqueous suspension and dissolved by the addition of a minimum of dilute sodium hydroxide to reach pH 8.0; a light insoluble material was filtered off, and then it was acidified with dilute hydrochloric acid, and the acid form again precipitated in the form of a beautiful white crystallization. It was filtered, washed carefully with water, and dried (mp=182°). TLC on Kieselgel gave a single spot of Rf 0.54 in the A system and a single spot also of Rf 0.39 in the B system. The sodium salt of this derivative can be obtained by neutralization of the aqueous suspension of the acid form, with dilute sodium hydroxide at pH 8–8.20. The limpid solution was then evaporated and dried under vacuum (NMR: CH₂—CH₃ (m) 1 ppm. —CH—(m) 2 H at 2.3 ppm, CH (m) 1 H at 4.8 ppm).

Example 7—N₂ (2-Ethyl) Butane Sulfonic Acid of 2,4-Diamino 5-(3,4,5-Trimethoxy Benzyl) Pyrimidine and its Sodium Salt

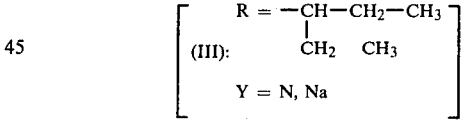

14.5 g (0.05 mole) of trimethoprime and 5.0 g (0.05 mole) of 2-ethyl butyraldehyde was added to 100 ml of pyridine, and then procedure was as in the preceding Examples. The crude product separated from the ether and dried was taken up again in water and placed in solution by the addition of dilute sodium hydroxide at pH 9.30. Some impurities were filtered off, then the acid form was reprecipitated by the addition of dilute hydrochloric acid to the filtrate to pH 2.20. Crystallization of the acid form was completed by cooling the suspension to 0° C. for some hours. By filtration and drying, the acid form of the derivative was obtained. TLC of the derivative gave a single spot of Rf 0.61 in the A system and 0.49 in the B system. Its melting point was 170° C. The alkaline form could be obtained by dispersing the acid derivative in water and then redissolving it by the addition of the minimum of dilute sodium hydroxide to pH 8.90–9.20. After evaporation at low temperature of the alkaline solution and drying, the desired derivative was obtained (NMR: CH$_3$—CH$_2$—(m) 10 H at 1.1 ppm, CH (m) 1 H at 2.2 ppm, CH (m) 1 H at 4.8 ppm).

Example 8—N$_2$ Phenyl Methane Sulfonic Acid of 2,4-Diamino 5-(3,4,5-Trimethoxy Benzyl) Pyrimidine and its Sodium Salt

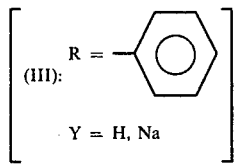

14.5 g (0.05 mole) of trimethoprime and 5.5 g (0.05 mole) of benzaldehyde was suspended in 100 ml of pyridine, and then the technique described in the preceding Examples was followed. The crude product was suspended in about 300 ml of water and supplemented with dilute sodium hydroxide to pH 8.0–9.0. After filtration of a light insoluble material, the acid form is reprecipitated by the addition of dilute hydrochloric acid in sufficient amount for pH 2.5. The acid form was filtered, washed, and dried. TLC of the acid derivative gave a single spot of Rf=0.52 in the A system and Rf=0.43 in the B system and mp=166° C. The alkaline form was obtained by treating the aqueous suspension of the acid form with the minimum amount of dilute sodium hydroxide to obtain complete solution, namely pH 8.40–8.50, and then by evaporating this solution to dryness the sodium salt of the desired derivative was obtained in the pure state. (NMR: arom (s) 5 H at 7.2 ppm, CH (m) at 4.8 ppm).

Example 9—N$_2$ (2-Chloro Phenyl) Methane Sulfonic Acid of 2,4-Diamino 5-(3,4,5-Trimethoxy Benzyl) Pyrimidine and its Sodium Salt

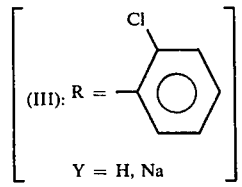

Successively, 14.5 g (0.05 mole) of trimethoprime and 7.0 g (0.05 mole) of 2-chloro benzaldehyde was added to 100 ml of pyridine; then operations were according to the technique described in the preceding Examples. The crude product was suspended in about 300 ml of water, then treated with 2 N sodium hydroxide to a pH 8.7–8.9. Light insoluble material was filtered off and the acid form reprecipitated by the addition of hydrochloric acid in a sufficient amount for pH 2.50.

It was kept at 0° C. for 24 hours to complete crystallization, then filtered, washed with water, and if necessary with alcohol. After drying, the pure acid form was obtained. TLC of the acid form gave a single spot of Rf 0.58 in the A system and 0.54 in the B system. This acid form can be treated in an aqueous medium with dilute sodium hydroxide to pH 8.10–8.20 to give the sodium form of the product which is isolated by evaporation and drying. mp=165° C. (NMR: arom (4H) (m) at 7.2 ppm—H (m) at 4.8 ppm.

Example 10—N$_2$ (3-Chloro Phenyl) Methane Sulfonic Acid of 2,4-Diamino 5-(3,4,5-Trimethoxy Benzyl) Pyrimidine and its Sodium Salt

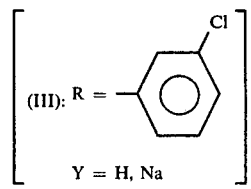

Successively 14.5 g (0.05 mole) of trimethoprime and 7.0 g (0.050 mole) of 3-chloro benzaldehyde was added to 100 ml of pyridine, and then procedure was as in the preceding Examples. The crude product was suspended in 350 ml of water and supplemented with 2 N sodium hydroxide to pH 8.10–8.60. A light insoluble material was filtered off, and then it was acidified with dilute hydrochloric acid to pH 2.25. The precipitate in acid form was filtered, washed with water, then with absolute ethanol. After drying, the desired derivative was obtained in the pure state. TLC on Kieselgel gave a single spot of Rf 0.59 in the A system and 0.57 in the B system. By alkalinization with dilute sodium hydroxide of the aqueous suspension of the acid form to the value of pH 8.60–8.70, the sodium salt of the desired derivative was obtained after evaporation and drying. mp=176° C. (NMR; arom 4 H (m) 7.2 ppm 1 H (m) at 4.8 ppm).

Example 11—N$_2$(4-Chloro Phenyl) Methane Sulfonic Acid of 2,4-Diamino 5-(3,4,5-Trimethoxy Benzyl) Pyrimidine and Its Sodium Salt

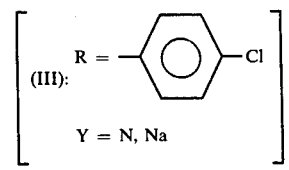

Successively, 14.5 g (0.05 mole) of trimethoprime and 7.0 g (0.05 mole) of 4-chlorobenzaldehyde were added successively into 100 ml of pyridine. After treatment by the usual technique, the crude product was resuspended in about 300 ml of water and it was brought to a pH 8.5–9.0 by the addition of dilute sodium hydroxide. A light insoluble material was filtered off, and then it was acidified to a pH 2.20 with dilute hydrochloric acid. The acid form of the derivative was filtered, then washed carefully with water and with absolute ethanol. After drying the desired derivative was obtained, as the acid form in the pure state. TLC of the product showed a single spot of Rf 0.62 in the A system and 0.56 in the B system. The acid form resuspended in water was converted into the sodium salt by the addition of dilute sodium hydroxide to pH 8.40–8.50. It was evaporated and dried to obtain the sodium form of the desired derivative, of mp 174° C. (NMR: 4H (arom) (m) at 7.3 ppm, H (m) at 4.8 ppm).

Example 12—N₂ (4-Nitro Phenyl) Methane Sulfonic Acid of 2,4-Diamino 5-(3,4,5-Trimethoxy Benzyl) Pyrimidine and Its Sodium Salt

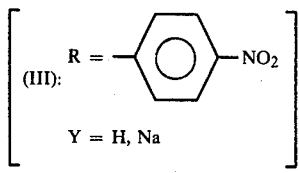

Successively 14.5 g of trimethoprime (0.05 mole and 7.5 g of 4-nitro-benzaldehyde was introduced successively into 100 ml of pyridine. After treatment by the usual technique, the crude product was resuspended in 400 ml of water and made alkaline with dilute sodium hydroxide to pH 10.0. A light insoluble material was filtered off and it was then acidified to pH 4.0 with dilute hydrochloric acid. The precipitate was filtered, then washed carefully with water and then with absolute ethanol. After drying, the desired derivative was obtained in the pure state in its acid form. TLC of the product gave only one spot of Rf 0.62 in the A system and 0.52 in the B system. The acid form was resuspended in water and dissolved by the addition of dilute sodium hydroxide of pH 8.80. After evaporation of the water under reduced pressure and drying, the sodium form of the desired derivative of mp=190° C. was obtained. (NMR:2 H (arom) m at 8.4 ppm, 2 H (arom) at 7.2 ppm, 1 H (m) at 4.8 ppm).

Example 13—N₂ (3-Nitro Phenyl) Methane Sulfonic Acid of 2,4-Diamino 5-(3,4,5-Trimethoxy Benzyl) Pyrimidine and Its Sodium Salt

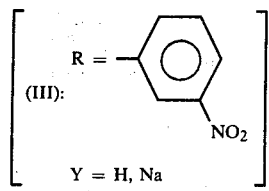

Successively, 14.5 g (0.05 mole) of trimethoprime and 7.5 g (0.05 mole) of 3-nitro benzaldehyde was dissolved in 100 ml of pyridine. After treatment by the usual technique, the product was suspended again in water, then made alkaline with dilute sodium hydroxide to a pH 9.0. A light insoluble material was filtered off, and then it was acidified to pH 2.5 with dilute hydrochloric acid. The precipitate was filtered off, washed with water and then with ethanol. After drying, the acid form of the desired derivative was obtained in the pure state mp 196° C. TLC of the product gave a single spot of Rf 0.56 in the A system and 0.46 in the B system. The acid form was resuspended in the proportion of about 3% in ethanol and redissolved by the addition of 2 N sodium hydroxide to pH 8.6-8.8. After evaporation and drying, the sodium form of the desired derivative of mp 178° C. was obtained (NMR:3 H (arom) m at 8.4 ppm, 1 H (arom) at 7.2 ppm, 1 H (m) at 4.8 ppm).

Example 14—N₂ (2-Nitro Phenyl) Methane Sulfonic Acid of 2,4-Diamino 5-(3,4,5-Trimethoxy Benzyl) Pyrimidine and Its Sodium Salt

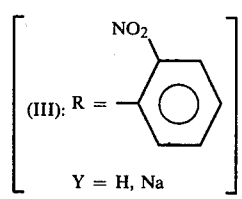

Successively, 29 g (0.1 M) of trimethoprime and 50.1 g (0.1 M) of orthonitrobenzaldehyde were introduced into 100 ml of pyridine, and then in one hour and a half, 70 g of sulfurous anhydride was introduced. After treatment by the usual technique, the crude product was resuspended in 400 ml of water and was brought to pH 8.80 with dilute sodium hydroxide. After filtration of a light insoluble material, it was reprecipitated by acidification with dilute hydrochloric acid. The precipitate was filtered off, washed with water and then with ethanol. After drying, the acid form of the desired derivative was obtained in the pure state with mp 180° C. TLC of the product gave a single spot Rf 0.55 in the A system and 0.45 in the B system. The acid form was resuspended in ethanol and redissolved by the addition of sodium hydroxide of pH 8.80. Evaporation and drying, gave the sodium form of the desired derivative, mp=173° C. (NMR:arom (m) 4 H at 7–8 ppm. —H (m) at 4.8 ppm).

Example 15—N₂ (2-Methoxy Phenyl) Methane Sulfonic Acid of 2,4-Diamino 5-(3,4,5-Trimethoxy Benzyl) Pyrimidine and Its Sodium Salt

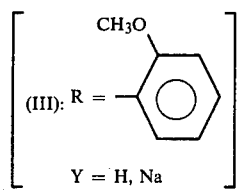

Successively, 14.5 g (0.05 mole of trimethoprime and 6.8 g (0.05 mole) of ortho anisaldehyde was added to 100 ml of pyridine. After the usual treatment, the crude product was resuspended in water and redissolved by the addition of dilute sodium hydroxide to pH 7.70–7.90. A light insoluble material was filtered off and it was acidified to about pH 2.2 with dilute hydrochloric acid. The precipitate was filtered off, washed with water, then abundantly with warm absolute ethanol; after drying, the pure acid form of the desired derivative of mp 150° C. was obtained. TLC of the product gave a single spot of Rf 0.58 in the A system and 0.44 in the B system. By a treatment with dilute sodium hydroxide of pH 8.8–8.9 of the acid form, the sodium salt was obtained which was isolated by evaporation of the solution (mp=165° C.). (NMR:OCH₃ (s) 3 H at 3.9 ppm, arom (m) 4 H at 7.2 ppm—H (m) at 4.8 ppm).

Example 16—N₂ (3-Methoxy Phenyl) Methane Sulfonic Acid 2,4-Diamino 5-(3,4,5-Trimethoxy Benzyl) Pyrimidine and Its Sodium Salt

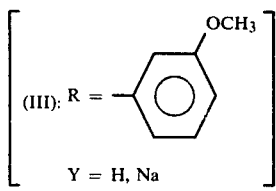

Successively 14.5 g (0.05 mole) and 6.8 g (0.05 mole) of meta anisaldehyde was added to 100 ml of pyridine, and then it was treated in the usual manner. The crude product was resuspended in 400 ml of water and dissolved by the addition of dilute sodium hydroxide at pH 8.10–8.20. After filtration of a light insoluble material, it was brought back to an acid medium by dilute hydrochloric acid to pH 2.4. The acid form precipitates, is filtered and washed with water then with absolute ethanol. After drying, the pure acid form of the desired derivative was obtained. TLC of the product gave a single spot of Rf 0.61 in the A system and 0.56 in the B system. The acid form was resuspended in water and treated with dilute sodium hydroxide to pH 8.10–8.20. The solution was evaporated to dryness under reduced pressure; after drying, the sodium form of the desired derivative of mp 192° C. was obtained. (NMR:4 H (arom) (m) 7.2 ppm —OCH₃ (3 H) (s) 4.0 ppm, H (m) at 4.8 ppm).

Example 17—N₂ (3,4,5-Trimethoxy Phenyl) Methane Sulfonic Acid 2,4-Diamino 5-(3,4,5-Trimethoxy Benzyl) Pyrimidine and Its Sodium Salt

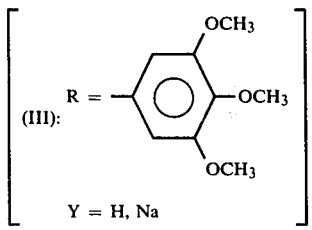

Successively, 14.5 g (0.05 mole) of trimethoprime and 7.5 g (0.05 mole) of 3,4,5-trimethoxy benzaldehyde were added into 100 ml of pyridine. After the usual treatment, the crude product was placed again in aqueous suspension and treated with dilute sodium hydroxide to pH 9.0. If necessary a light insoluble material was filtered off, then the filtrate was acidified to a pH 2.5 by the addition of dilute hydrochloric acid. The precipitate was filtered, washed carefully with water, and with hot ethanol. After drying, the pure acid form of the desired derivative was obtained. TLC of the product gave a single spot of Rf 0.65 in the A system and 0.49 in the B system. The acid form can be treated in water by dilute sodium hydroxide to pH 9.0. By evaporation of the solution under reduced pressure, then drying, the sodium form of the desired derivative of mp 188° C. was obtained. (NMR 2 H (arom) 6.60 (s)—6 H (s) —OCH₃ at 3.60 ppm, H (m) at 4.8 ppm).

Example 18—N₂ (3,4-Dioxy Methylene Phenyl) Methane Sulfonic Acid of 2,4-Diamino 5-(3,4,5-Trimethoxy Benzyl) Pyrimidine and Its Sodium Salt

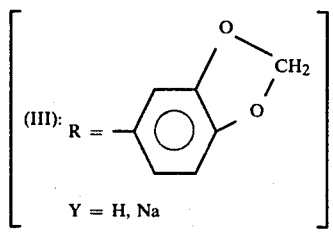

Successively, 14.5 g (0.05 mole) of trimethoprime and 7.5 g (0.05 mole) of piperonal was introduced into 100 ml of pyridine. After treatment by the usual technique, the product was resuspended in 300 ml of water and made alkaline with dilute sodium hydroxide to pH 9.0. A light insoluble material was filtered off, and then acidified with dilute hydrochloric acid to pH 2.5. The precipitate which appeared was filtered, washed abundantly with water and then with ethanol. After drying, the acid form of the desired derivative was obtained. TLC of the product gave a single spot of Rf 0.53 in the A system and 0.44 in the B system. The aqueous suspension of the acid form can be treated by the addition of dilute sodium hydroxide at pH 8.90–9.0. The clear solution was evaporated under reduced pressure, then dried to give the sodium form of the desired derivative, of mp 165° C. (NMR:3 H (arom) m at 7.2 ppm —CH₂—2 H (s) at 6.0 ppm—1 H (m) at 4.8 ppm).

Example 19—N₂ 2-Furyl Methane Sulfonic Acid of 2,4-Diamino 5-(3,4,5-5-(3,4,5-Trimethoxy Benzyl) Pyrimidine and Its Sodium Salt

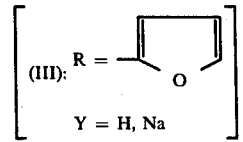

39.0 g (0.40 mole) of furaldehyde and 116 g (0.4 mole) of trimethoprime were added successively to 800 ml of pyridine and then sulfurous anhydride were bubbled through at the rate of 80 g/h for 4 hours. The temperature rose spontaneously from 20° to 55° C. After cooling, it was run into 5 liters of ether and the precipitate filtered. The dried crude product was resuspended in 12 volumes of water and treated with dilute sodium hydroxide to pH 8.70. After filtration of a light insoluble substance, the filtrate was acidified with dilute hydrochloric acid to pH 2.5. The insoluble acid form was filtered off and washed carefully with water and then with ethanol. After drying, the acid form of the desired derivative of mp 163° C. was obtained. The TLC of the product gave a single spot of Rf 0.46 in the system A and 0.32 in the system B. By treatment with dilute sodium hydroxide of the aqueous suspension of this acid form to pH 8.70, after evaporation under reduced pressure and drying, the sodium form of the desired derivative of mp=125° C. was obtained (NMR:3 H (arom) (m) 6.5 and 7.5 ppm—CH—1 H (m) to 4.8 ppm).

Example 20—N₂ (2-Thienyl) Methane Sulfonic Acid of 2,4-Diamino 5-(3,4,5-Trimethoxy Benzyl) Pyrimidine and Its Sodium Salt

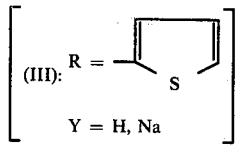

Successively, 14.5 g (0.05 mole) of trimethoprime and 4.6 g (0.05 mole) of 2 thienyl aldehyde was added to 100 ml of pyridine, and then the treatment was in accordance with Example 6.

The crude product was replaced in aqueous suspension a and treated with dilute sodium hydroxide to pH 8.40–8.60. After filtration of a light insoluble substance, the filtrate was treated with dilute hydrochloric acid to pH 2.5. The precipitate which appeared was filtered off, washed with water, and then with ethanol. After drying, the acid form of the desired derivative in its pure state was obtained. The TLC of the product gave a single spot of Rf 0.61 in the system A and 0.43 in the system B. By treatment of the aqueous suspension in the acid form with dilute sodium hydroxide to a pH 8.4–8.60, after evaporaton drying, the sodium salt of the desired derivative of mp 152° C. was obtained (NMR:arom 2 H (m) at 6.2 ppm—1 H (m) at 7.8 ppm; H (m) at 4.8 ppm).

Example 21—N₂ (4-Hydroxy 3-Methoxy) Phenyl Methane Sulfonic Acid of 2,4-Diamino 5-(3,4,5-Trimethoxy Benzyl) Pyrimidine and Its Sodium Salt

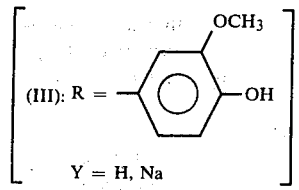

Successively, 14.5 g (0.05 mole) of trimethoprime and 7.5 g (0.05 mole) of vanillin were added to 100 ml of pyridine, and then the procedure was in accordance with the preceding Example. The crude product was replaced in aqueous suspension an and treated with dilute sodium hydroxide to a pH of 7.80–8.00. A light insoluble substance was filtered off, and then the acid form was reprecipitated by the addition of dilute hydrochloric acid at pH 2.5. The precipitate was filtered, washed carefully with water and then with ethanol. After drying, the pure acid form was obtained. TLC of the product gave a single spot of Rf 0.29 in the A system and 0.27 in the B system. By treatment of the aqueous suspension in the acid form with dilute sodium hydroxide to pH 7.70, there was obtained, after evaporation and drying, the sodium form of the desired derivative mp 160° C. (NMR:5 H (arom) (m) at 6.8–7.2 ppm —CH—1 H at 4.8 ppm).

Example 22—N₂ 2-Pyridyl Methane Sulfonic Acid of 5-(3,4,5-Trimethoxy Benzyl) 2,4-Diamino Pyrimidine

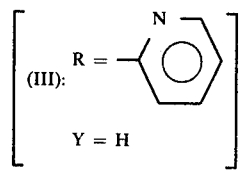

14.5 g (0.05 mole) of trimethoprim and 5.5 g (0.05 mole) of 2-pyridine carboxaldehyde were introduced successively into 100 ml of pyridine, then procedure was according to that of Example 6. The crude product was then dispersed in water acidified with precaution to pH 2.8 with dilute hydrochloric acid. A light insoluble substance was filtered off and the filtrate was brought back slowly to pH 4.60 with dilute sodium hydroxide. The sulfonic acid form of the desired derivative precipitates in the pure state; after filtration, washing with water and with ethanol, the desired derivative in the pure state of mp 185° C. was obtained. TLC of the product gave a single spot of Rf 0.45 in system A and 0.2 in system B. The desired derivative insoluble at pH 5.6 has an amphoteric nature and can be dissolved at slightly acid pH between pH 3 and pH 5 in slightly alkaline pH between pH 7 and pH 9. (NMR:5 H (arom) (m) at 6.8–7.2 ppm —CH—1 H at 4.8 ppm).

Example 23—N₂ Cyclohexyl Methane Sulfonic Acid of 5-(3,4,5-Trimethoxy Benzyl) 2,4-Diamino Pyrimidine and Its Sodium Salt

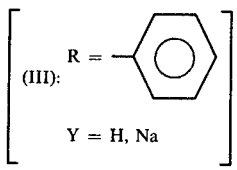

Successively, 14.5 g (0.05 mole) of trimethoprime and 5.6 g (0.05 mole) of cyclohexane-carboxaldehyde was added successively to 100 ml of pyridine, and then treated according to Example 6. The aqueous suspension of the crude product was then treated with dilute sodium hydroxide to the pH of 10. After filtration of a light insoluble substance, the filtrate was rapidly acidified to pH 3.0. After filtration of the precipitate and washing with water and with hot ethanol, after drying, the acid form of the desired derivative of mp 162° C. was obtained. TLC of the product gave a single spot of Rf 0.9 in the system A and of 0.55 in the system B.

The sodium form of the desired derivative can be obtained by treatment of the aqueous suspension of the acid form with dilute sodium hydroxide at pH 9.0, followed by evaporation at low temperature of the solution, and drying (NMR:11 (H) (m) at 1.5–2.0 ppm, CH (1HO (m) at 4.8 ppm).

Example 24—$N_2$ (3-Ethoxy 4-Hydroxy) Phenyl Methane Sulfonic Acid of 5-(3,4,5-Trimethoxy Benzyl) 2,4-Diamino Pyrimidine and Its Alkali Metal or Organic Amine Salts

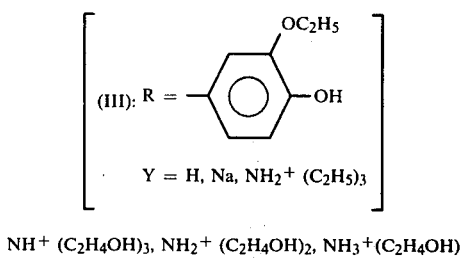

$NH^+ (C_2H_4OH)_3$, $NH_2^+ (C_2H_4OH)_2$, $NH_3^+(C_2H_4OH)$

(a)—(Y=H)

Successively, 145 g (0.5 mole) of trimethoprime and 83 g (0.5 mole) of vanillin was added to 500 ml of pyridine, and about 130 g of sulfurous anhydride was added in three hours. The temperature of the reaction mixture rose spontaneously between 40° and 50° C. from the start of the introduction and was held there until the end of the reaction. It was left for 24 hours at ordinary temperature. Then the reaction mixture was poured into a large volume of ether, the precipitate which appeared was filtered off and washed with ether. The crude product was then dispersed in water and treated with dilute sodium hydroxide to pH 9.30-9.40. A light insoluble substance was filtered off, then the product was reprecipitated by the addition of hydrochloric acid to the alkaline solution to pH 2-3. It was filtered, washed with water, and then with ethanol. After drying, the acid form of the desired derivative of mp 145° C. was obtained. TLC of the product gave a single spot of Rf 0.50 in the system A and Rf 0.40 in system B.

(b)—(Y=Na)

The sodium salt of the product was obtainable by treatment of the aqueous suspension of the acid form with dilute sodium hydroxide to a pH of 8.80. After evaporation of the solution under reduced pressure and drying, the sodium salt of the desired derivative of mp 170° C. was obtained.

(NMR:1 H (s) at 8.5 ppm—3 H (arom) (m) at 7.2 ppm—2 H —$OCH_2$ (1) at 3.9 ppm—3 H (t) $CH_3$ at 1 ppm).

(c)—(Y=$NH^+ (C_2H_5)_3$)

The triethylamine salt of the desired derivative was obtainable by treatment on the aqueous alcohol suspension (50/50) of the acid form of pure triethylamine to pH 8.90-9.0. The clear solution was evaporated under reduced pressure. After drying, the triethylamine salt of the desired derivative of mp 120° C. was obtained.

(d)—(Y=$NH_3^+ (C_2H_4OH)$)

The monoethanolamine salt was obtainable by treating 10 g of the acid form in suspension in 100 ml of aqueous 50% ethanol with a slight excess of monoethanolamine. The resulting solution was evaporated to dryness under reduced pressure. The residue was taken up again in an acetone benzene mixture. mp 120° C. (dec).

(e)—(Y=$NH_2^+(C_2H_4OH)_2$)

The diethanolamine salt was obtainable by treating as above the acid form with a slight excess of diethanolamine; the salt of mp 125° C. (dec) was obtained.

(f)—(Y=$NH^+(C_2H_4OH)_3$)

In the same way the triethanolamine salt was obtained by treating the acid form according to (d) with a slight excess of triethanolamine; in this way the salt of mp 107° C. was obtained.

EXAMPLE 25—$N_2$(2-HYDROXY) PHENYL METHANE SULFONIC ACID OF 5-(3,4,5-TRIMETHOXY BENZYL) 2,4-DIAMINO PYRIMIDINE AND ITS ALKALI METAL SALTS OR ITS AMINE SALTS

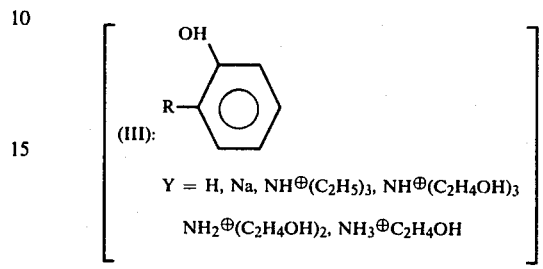

(a)—(Y=H)

Successively, 29.0 g (0.1 mole) of trimethoprime and 13.0 g of salicylaldehyde was added to 170 ml of pyridine, then 80 to 90 g of sulfurous anhydride was introduced in about 3 hours. The temperature of the reaction mixture was maintained spontaneously between 40° and 50° C. After 24 hours with ordinary temperature, the medium was run into excess ether, the resulting precipitate was filtered off, washed with ether and then dried. The crude product was restored into aqueous suspension and made alkaline to pH 9.30 with dilute sodium hydroxide. After filtration of the insoluble material, the filtrate was acidified to pH 2.0 with dilute hydrochloric acid, and the acid form precipitated. It was filtered off, washed abundantly with water, and then ethanol. After drying, the acid form of the desired derivative mp 145° C. was obtained. TLC of the product gave a single spot of Rf 0.40 in the A system and Rf 0.30 in the B sytem.

(b)—(Y=Na)

The sodium salt of the desired derivative was obtainable by treatment of the aqueous suspension of the acid form with dilute sodium hydroxide to pH 8.90. After evaporation and drying, the sodium salt of the desired derivative was obtained.

(c)—(Y=$NH^+(C_2H_5)_3$)

The triethylamine salt of the product was obtainable by treating the aqueous alcohol suspension (50/50) of the acid form with triethylamine at pH 8.90. After evaporation of the solution under reduced pressure, and then drying, the triethylamine of the desired derivative was obtained (mp 113° C.).

(d)—(Y=$NH_3^+(C_2H_4OH)$)

The monoethanolamine salt was obtained by treating 10 g of the acid form in 100 ml of 50% of aqueous ethanol with a slight excess of monoethanolamine. After evaporation under reduced pressure and taking up again with acetone, the monoethanolamine salt of the desired derivative mp 80°/90° C. (dec), was obtained.

(e)—(Y=$NH_2^+(C_2H_4OH)_2$)

The diethanolamine salt obtained by the above process using a slight excess of diethanolamine mp 100°/110° C. (dec).

(f)—(Y=$NH^+(C_2H_4OH)_3$)

The triethanolamine salt was obtained by (d), using triethanolamine in slight excess mp 110° C. (dec).

Elementary analysis of the following elements have been carried out on all the products mentioned: C, H N, S and Na. These analyses all correspond (to within 0.3%) to the theoretical data.

Among the spectrographic signals by nuclear magnetic resonance of the $^1$H, only the signals characteristic of the radical R have been mentioned. The signals of the common unit being the following (solution/DMSO d$^6$ of the sodium salts with respect to the T.M.S.) 7.23 ppm aromatic 1 H (s) of pyrimidine; 6.55 ppm aromatic 2 H (s) 6.44 ppm 2 H (s wide) of NH$_2$; 5.90 ppm 1 H (s wide) of NH; 3.75 ppm 6 H (s)—OCH$_3$ at 3 and 5; 3.64 ppm 3 H (s)—OCH$_3$ at 4; 3.54 ppm 2 H (s)—CH$_2$—.

REPORT OF PHARMACOLOGICAL TESTS CARRIED OUT WITH PRODUCTS ACCORDING TO THE INVENTION

Pharmacological studies were directed on the one hand to toxicity, and on the other hand to antibacterial activity.

A—Toxicity

From the point of view of immediate toxicity, it emerges that the derivatives according to the invention are of very little toxicity and especially much less than the initial 2,4-diamino pyrimidines. The lethal doses (LD 50) obtained by oral or intravenous administration in the mouse are very high.

The comparative values collected in Table I below examplify these differences in toxicity; numeric measurements were carried out on homogeneous batches of 10 female SWISS IOPS mice, aged 4 weeks and of average weight 18 to 20 g.

TABLE I

| LD 50 mg/kg | Tri-metho-prime | Deriva-tive of ex. 18 | Deriva-tive of ex. 15 | Deriva-tive of ex. 24 f | Deriva-tive of ex. 19 |
|---|---|---|---|---|---|
| By mouth | 4000 | >12,000 | >12,000 | >12,000 | >12,500 |
| I.V. | 120 | | 1,000 | 1,000 | 900 |

B—Antibacterial activity

The antibacterial activity of the derivatives according to the invention were tested in vitro by determining the inhibiting minimum concentrations (I.M.C.) on different germs. The compared values of the I.M.C. of the various compounds related to those of trimethoprime taken as a reference, as well as the ratio R representing $$\text{activity} \times \frac{\text{Derivative molecular weight}}{\text{Trimethoprime molecular weight}}$$

are collected in Table II below.

TABLE II

| EXAMPLE | OXOIDE COLI MEDIUM 4 | | MULLER HINTON COLI MEDIUM 4 | | MULLER HINTON BACIL PUMILUS MEDIUM | |
|---|---|---|---|---|---|---|
| | % activity with respect to the base | % activity with respect to the base corrected by molecular weight | % activity with respect to the base | % activity with respect to the base corrected by molecular weight | % activity with respect to the base | % activity with respect to the base corrected by molecular weight |
| Example 1 | 17.1 | 24 | 0.3 | 0.4 | 0.1 | — |
| Example 2 | 4 | 5.8 | 4.3 | 6.2 | 2.8 | 4 |
| Example 3 | 18.35 | 28 | 4.55 | 10.8 | 2.9 | 6.8 |
| Example 4 | 12.9 | 20 | 14.1 | 22 | 11.8 | 18 |
| Example 5 | 18.4 | 29 | 23.3 | 37 | 19.4 | 30 |
| Example 6 | 18.8 | 32 | 15.75 | 27 | 16.6 | 28 |
| Example 7 | 14 | 23 | 15.5 | 25 | 14 | 23 |
| Example 8 | 13.3 | 21 | 10.2 | 16.4 | 18.4 | 26 |
| Example 9 | 14.7 | 26 | 13.3 | 23 | 14.1 | 25 |
| Example 10 | 14.1 | 25 | 11.6 | 20 | 10.4 | 18 |
| Example 11 | 25.6 | 45 | 17.6 | 31 | 23 | 41 |
| Example 12 | 11.7 | 21 | 18.1 | 32 | 11.9 | 22 |
| Example 13 | 32.5 | 59 | 17.2 | 31 | 23.2 | 42 |
| Example 14 | 10.6 | 19 | 13.9 | 25 | 11.0 | 20 |
| Example 15 | 64 | 107 | 47 | 73 | 60 | 106 |
| Example 16 | 13.2 | 23 | 16.8 | 29 | 10.7 | 19 |
| Example 17 | 34.8 | 68 | 24.3 | 48 | 42.7 | 84 |
| Example 18 | 27 | 48 | 14.85 | 26 | 21.4 | 38 |
| Example 19 | 58.4 | 95 | 69.4 | 112 | 49.5 | 80 |
| Example 20 | 62.6 | 105 | 73.5 | 123 | 83.4 | 140 |
| Example 21 | 49.8 | 90 | 43.3 | 79 | 34.6 | 63 |
| Example 24b | 48.7 | 93 | 43.9 | 84 | 42.2 | 79 |
| Example 24d | 13.1 | 26 | 23.2 | 46 | 37.0 | 74 |
| Example 24e | 21.3 | 46 | 40.0 | 86 | 40.0 | 86 |
| Example 24f | 27.4 | 63 | 40.3 | 92 | 31.8 | 73 |
| Example 25c | | | 57 | 116 | | |
| Example 25d | 28.3 | 53 | 45.4 | 85 | 55.5 | 104 |
| Example 25e | 36.6 | 74 | 45.8 | 93 | 75.8 | 154 |
| Example 25f | 38.3 | 84 | 55.4 | 120 | 73.1 | 159 |

The compounds according to the invention are powerful antibacterial agents; moreover, they potentiate the antibacterial action itself of the sulfamides in the treatment of bacterial infections in particular in the respiratory, digestive, urinary or otorhinolaryngological fields. By way of example, the associations with sulfamides like sulfadiazine, sulfamonomethoxine, sulfadimethoxine, sulfamethoxazol, sulfamoxol, 2-sulfa 2,4-dimethyl isoxazole and 4-sulfanilamido 5,6-dimethoxy pyrimidine may be mentioned. The compounds of formula III can be combined with the aforesaid sulfamides in variable proportions ranging from 1:1 to 1:5. The unit dose of active principle corresponding to the products of formula III may range from 50 to 100 mg.

As emerges from the foregoing, the invention is in no way limited to those of its modes of practice, embodiments, or uses which have just been described more explicitly; it encompasses, on the contrary, all modifications which may come to the spirit of the technician skilled in the art, without deparing from the framework or the scope of the present invention.

We claim:

1. Novel soluble $N_2$ substituted derivative of 2,4-diamino 5-benzyl pyrimidine corresponding to the formula III:

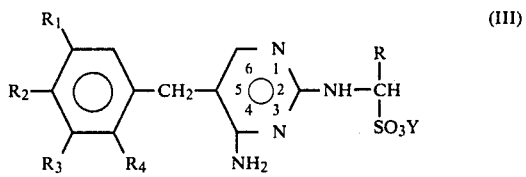

in which:
$R_1$, $R_2$, $R_3$, $R_4$ which may be identical or different, represent a hydrogen atom, a halogen atom or an alkyl, thioalkyl, alkoxy or benzyloxy-,alkyloxyalkoxy group;
Y represents a hydrogen atom, an alkali metal or a pharmaceutically compatible organic base, and
R represents a hydrogen atom or a linear or branched alkyl radical of 1 to 7 carbon atoms, a cycloalkyl radical of 5 to 8 carbon atoms, an aromatic nucleus possibly substituted by halogen, nitro-, hydroxyl, dialkylamino-, alkoxy-, alkyl from $C_1$ to $C_3$, two adjacent substituents being able to constitute an alkyldioxy-ring or, a heterocyclic ring of furane, thiophene, or pyridine.

2. Derivative according to claim 1, wherein the substituent on the $N_2$ atom is the methane sulfonic radical or its sodium salt.

3. Derivative according to claim 1, wherein the substituent on the $N_2$ atom is the ethane sulfonic radical or its sodium salt.

4. Derivative according to claim 1, wherein the substituent on the $N_2$ atom is the n-butane sulfonic radical.

5. Derivative according to claim 1, wherein the substituent on the $N_2$ atom is the 2-methyl propane sulfonic radical.

6. Derivative according to claim 1, wherein the substituent on the $N_2$ atom is the 2,2-dimethyl propane sulfonic radical.

7. Derivative according to claim 1, wherein the substituents on the $N_2$ atom is the 2,3-dimethyl pentane sulfonic radical.

8. Derivative according to claim 1, wherein the substituent on the $N_2$ atom is the 2-ethyl butane sulfonic radical.

9. Derivative according to claim 1, wherein the substituent on the $N_2$ atom is the phenyl methane sulfonic radical.

10. Derivative according to claim 1, wherein the substituent on the $N_2$ atom is the (2-chloro) phenyl methane sulfonic radical.

11. Derivative according to claim 1, wherein the substituent on the $N_2$ atom is (3-chloro) phenyl methane sulfonic radical.

12. Derivative according to claim 1, wherein the substituent on the $N_2$ atom, is the (4-chloro) phenyl methane sulfonic radical.

13. Derivative according to claim 1, wherein the substituent on the $N_2$ atom is the (4-nitro)phenyl methane sulfonic radical.

14. Derivative according to claim 1, wherein the substituent on the $N_2$ atom is the (3-nitro) phenyl methane sulfonic radical.

15. Derivative according to claim 1, wherein the substituent on the $N_2$ atom is the (2-nitro) phenyl methane sulfonic radical.

16. Derivative according to the claim 1, wherein the substituent on the $N_2$ atom is the (2-methoxy) phenyl methane sulfonic radical.

17. Derivative according to claim 1, wherein the substituent on the $N_2$ atom is the (3-methoxy) phenyl methane sulfonic radical.

18. Derivative according to claim 1, wherein the substituent on the $N_2$ atom is the (3,4,5-trimethoxy) phenyl methane sulfonic radical.

19. Derivative according to claim 1, wherein the substituent on the $N_2$ atom is the (3,4-methylenedioxy) phenyl methane sulfonic radical.

20. Derivative according to claim 1, wherein the substituent on the $N_2$ atom is the 2-furyl methane sulfonic radical or its sodium salt.

21. Derivative according to claim 1, wherein the substituent on the $N_2$ atom is the 2-thienyl methane sulfonic radical or its sodium salt.

22. Derivative according to claim 1, wherein the substituent on the $N_2$ atom is the (2-methoxy 4-hydroxy) phenyl methane sulfonic radical.

23. Derivative according to claim 1, wherein the substituent on the $N_2$ atom is the 2-pyridyl methane sulfonic radical or its or basic salts.

24. Derivative according to claim 1, wherein the substituent on the $N_2$ atom is the cyclohexylmethane sulfonic radical or its sodium salt.

25. Derivative according to claim 1, wherein the substituent on the $N_2$ atom is the (3-ethoxy 4-hydroxy) phenyl methane sulfonic radical, its sodium salt or its amine salts.

26. Derivative according to claim 1, wherein the substituent on the $N_2$ atom is the (2-hydroxy) phenyl methane sulfonic radical or its sodium salt or its amine salts.

27. Process for the preparation of products according to claim 1, comprising reacting in a suitable solvent such as pyridine, particularly, a derivative of 2,4-diamino 5-benzyl pyrimidine, with an aldehyde and sulfurous anhydride, and then isolating the product of the reaction.

28. Process according to claim 27, wherein the amounts of 2,4-diamino 5-benzyl pyrimidine and of aldehyde, are stoichiometric, whilst the sulfurous anhydride is used in excess.

29. Process according to claim 27, wherein the product of the reaction is isolated by dilution of the reaction medium with a solvent miscible with pyridine.

30. Process according to claim 28, wherein the product of the reaction is isolated by dilution of the reaction medium with a solvent miscible with pyridine.

31. Process according to claim 29 wherein said solvent is ether or a hydrocarbon.

32. Process according to claim 30, wherein said solvent is ether or a hydrocarbon.

33. Process according to claim 27, wherein the product isolated is in addition purified by washing with aqueous alcohol.

34. Process according to claim 28, wherein the product isolated is in addition purified by washing with aqueous alcohol.

35. Process according to claim 29, wherein the product isolated is in addition purified by washing with aqueous alcohol.

36. Medicament useful in human and/or veterinary medicine against bacteria, containing 50–1000 mg of at least one compound according to claim 1 in the pure state or in association with one or several other active principles and one or several compatible and pharmaceutically acceptable adjuvants or diluents.

37. Method of treating humans and/or animals suffering from bacterial infections, particularly in the respiratory, digestive, urinary or otorhinolaryngological fields, optionally associated with a sulfamide treatment comprising administering to the human or animal an effective dose of at least one compound according to claim 1.

38. Method of treatment according to claim 37, wherein the unit dose of active principle corresponding to the products of formula III is in the range from 50 to 1,000 mg.

39. Method of treatment according to claim 37, wherein the compound of formula III is combined with sulfamides in proportions ranging from 1:1 to 1:5.

* * * * *